(12) United States Patent
Sugano et al.

(10) Patent No.: US 9,376,478 B1
(45) Date of Patent: Jun. 28, 2016

(54) DNA AND RECOMBINANT PLASMID

(75) Inventors: Haruo Sugano, Tokyo (JP); Masami Muramatsu, Tokorozawa (JP); Tadatsugu Taniguchi, Tokyo (JP)

(73) Assignee: JURIDICAL FOUNDATION, JAPANESE FOUNDATION FOR CANCER RESEARCH, Tokyo (JP)

( * ) Notice: Subject to any disclaimer, the term of this patent is extended or adjusted under 35 U.S.C. 154(b) by 0 days.

(21) Appl. No.: 08/463,757

(22) Filed: Jun. 5, 1995

Related U.S. Application Data

(60) Division of application No. 08/400,179, filed on Mar. 6, 1995, now Pat. No. 5,514,567, which is a continuation of application No. 06/389,922, filed on Jun. 18, 1982, now abandoned, which is a division of application No. 06/201,359, filed on Oct. 27, 1980, now Pat. No. 5,326,859.

(30) Foreign Application Priority Data

Oct. 30, 1979 (JP) ..................................... 79-139289
Mar. 19, 1980 (JP) ..................................... 80-33931

(51) Int. Cl.
*C07K 14/565* (2006.01)

(52) U.S. Cl.
CPC .................................... *C07K 14/565* (2013.01)

(58) Field of Classification Search
USPC ............. 435/69.51, 811; 536/23.52; 530/351; 514/12; 424/85.4
See application file for complete search history.

(56) References Cited

PUBLICATIONS

Tanaguchi et al. Gene 10: 11-15, 1980.
Houghton. Nature 285: 536, 1980.
Derynck et al. Nature 285: 542-549, 1980.
Research Disclosure #18309, Jul. 1979.
Tanaguchi et al. Proc. Japan Acad. 55(B), Nov. 12, 1979, Dec. 8, 1980.
Tanaguchi et al. Proc. Natl. Acad. Sci. (USA), 77(7): 4003, Jul. 1980.

*Primary Examiner* — James Martinell
(74) *Attorney, Agent, or Firm* — Tarter Krinsky & Drogin LLP

(57) ABSTRACT

Disclosed is a recombinant plasmid having a gene which encompasses at least the entire coding region of human fibroblast interferon messenger RNA and a method for preparing such plasmid.

14 Claims, 1 Drawing Sheet

DNA AND RECOMBINANT PLASMID

This application is a divisional of application Ser. No. 08/400,179, filed of Mar. 6, 1995, now U.S. Pat. No. 5,514,567 which is a continuation of application Ser. No. 06/389,922, filed on Jun. 18, 1982 (abandoned), which is a divisional of application Ser. No. 06/201,359 filed on Oct. 27, 1980, now U.S. Pat. No. 5,326,859.

BACKGROUND OF THE INVENTION

The present invention relates to a DNA which codes for a polypeptide with interferon activity and a recombinant plasmid containing the DNA. The present invention also pertains to a microorganism containing the recombinant plasmid.

Interferon is a glycoprotein (molecular weight approx. 20,000) with antiviral activity, discovered by Isaacs and Lindemann in 1957. Subsequent studies have indicated antitumor activity of the substance in addition to antiviral activity and hence a wide clinical application of this substance is expected. For instance, it has been reported that interferon may be effectively administered to treat various viral diseases, osteosarcoma and mammary carcinoma.

However, because of its high species-specificity, only the interferon derived from human cells can be used for human application. At present, the interferon which is being used for administration has a relative activity of about $10^6$ (International units) per 1 mg, which corresponds to a purity of about 0.1-0.01%.

Moreover, the use of the interferon is quite limited because of difficulties in mass-production. At present even for the interferon requirement for clinical tests ($10^{13}$ units per year), the supply is only about 1%. For these reasons, development of technology to produce human interferon in high purity, with ease and in large quantities is in demand.

To this end, a novel technique has been developed for producing interferon with ease and in a large quantity by inserting a human interferon gene into a plasmid DNA (for instance plasmid DNA derived from *Escherichia coli*) with recombinant DNA (deoxyribonucleic acid) technology.

SUMMARY OF THE INVENTION

In accordance with the present invention, a DNA which codes for a polypeptide with interferon activity is prepared using the human interferon messenger RNA as a template and a novel recombinant plasmid containing the DNA is prepared. In addition, the recombinant plasmid may be inserted into a host microorganism.

The DNA which codes for a polypeptide with interferon activity and the recombinant plasmid containing the DNA have been obtained for the first time by the present inventors. The DNA and the recombinant plasmid may be used, inter alia, for amplification of human interferon in bacteria such as *Escherichia coli*. Such bacteria are then useful for the production of human interferon in large quantities at low cost.

The DNA and the recombinant plasmid of the present invention are prepared by the following general procedure.

First, cytoplasmic RNA is extracted from (1) human fibroblast, MG63 cells or others induced by poly(I):poly(C) which is a double stranded RNA composed of polyinosinic acid and polycytidylic acid or other inducers, (2) human leucocyte, lymphoblastic cells, NAMALWA cells or others induced by Sendai virus or other inducers, or (3) lymphocytes induced by various mitogens or other inducers. From this RNA, the human interferon messenger RNA (hereinafter messenger RNA is referred to as mRNA) containing poly A (polyadenylic acid) is isolated. A double stranded DNA is synthesized, for example, by reverse transcriptase, with the mRNA preparation having high interferon mRNA activity, as a template. A recombinant is obtained by inserting the synthesized DNA into a vector DNA such as *Escherichia coli* plasmid DNA by the technique of in vitro DNA recombination. The recombinant is labelled with a radio isotope for use as a probe. Recombinant plasmids having an inserted portion which is complementary to the human interferon mRNA are selected. The DNA which codes for a polypeptide with interferon activity is recovered from the recombinant plasmid and the base sequence of the DNA is determined.

DETAILED DESCRIPTION OF THE PRESENT INVENTION

Figure 1A:
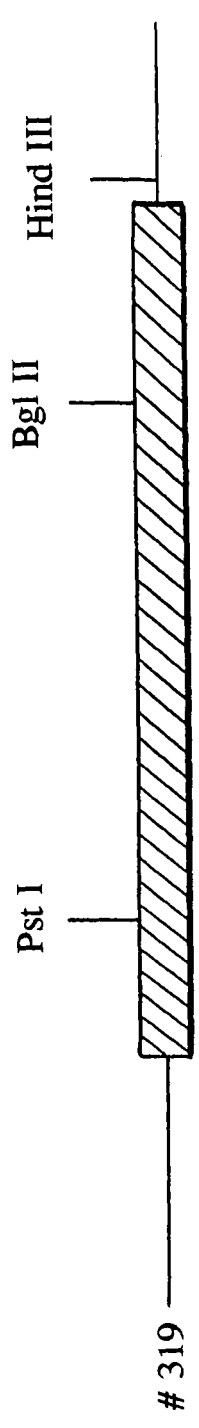
FIG. 1 illustrates restriction endonuclease maps of:
(a) a gene which shows complementarity to the human fibroblast interferon mRNA in the recombinant #319 used to make a novel recombinant plasmid #319-13; and
(b) a gene which shows complementarity to the human fibroblast interferon mRNA in the novel recombinant plasmid 4319-13.

The present invention relates to a DNA which codes for a polypeptide with interferon activity, a recombinant plasmid containing the DNA and a microorganism containing the recombinant plasmid.

The DNA of the present invention may be a cloned DNA showing complementarity to the human interferon mRNA, a cloned DNA which codes for a polypeptide with interferon activity or a cloned DNA which codes for human interferon polypeptide. Especially a DNA which encompasses the entire coding region of the human fibroblast interferon (i.e. human $\beta_1$ interferon) mRNA is a preferred example of the DNA of the present invention.

The recombinant plasmid of the present invention is a recombinant plasmid wherein the DNA mentioned above is inserted in a vector DNA such as pBR322, pCR1 or, pMB9.

The recombinant plasmids named #319 and #319-13 are preferred examples of a recombinant plasmid according to the invention.

The DNA and the recombinant plasmid are inserted in a host microorganism and the transformant can be used to produce a substance having interferon activity.

As the host microorganism, *Escherichia coli* χ1776 is preferably used.

A example of the processes of producing the DNA, the recombinant plasmid and the transformant of the present invention is as follows.

First, human fibroblasts may be obtained from fetus-derived foreskin, or the like. A small amount of interferon is then added to a culture fluid of human fibroblasts to prime the interferon synthesis by human fibroblasts, to which poly(I):poly(C) is added to induce the synthesis of interferon mRNA. Cycloheximide is added simultaneously to increase the level of interferon mRNA. At an appropriate time (about 4 hours) after the human fibroblasts are superinduced in the above manner, cells are collected and destroyed and the nuclei are removed. Cytoplasmic total RNA is extracted with phenol, or the like. The RNA can also be extracted by destroying the whole cells, extracting both DNA and RNA with, for example, phenol, and degrading and removing the DNA with DNAase.

Further, interferon mRNA can also be extracted from MG63 cells induced by poly(I): poly(C) or other inducers, human leucocyte or lymphoblastic cells induced by Sendai virus or other inducers, and lymphocytes induced by various mitogens or other inducers.

The thus extracted RNA is dissolved in a salt solution of NaCl or KCl at a high concentration such as 0.5M and put on a column of oligo (dT) cellulose to adsorb mRNA having poly(A) on the column. Elution is carried out with water, a salt solution at a low concentration such as 10 mM Tris-HCl buffer, or the like to isolate mRNA having poly(A).

The isolated mRNA is fractionated by sucrose density gradient centrifugation. Interferon mRNA activity in each fraction is checked by determining interferon activity (antiviral activity) of the protein which is synthesized in oocytes of African claw toad (*Xenopus laevis*) after micro-injecting a part of the mRNA in each fraction. The determination of interferon activity is carried out according to the method described in Japan J. Microbiol. 18, 449-456, (1974).

Then, a DNA showing complementarity to the mRNA is synthesized in vitro by a reverse transcriptase, which is obtained from avian myeloblastosis virus, using, as the template, an mRNA having the highest interferon mRNA activity.

The synthesis is carried out as follows.

An mRNA is reacted at an appropriate temperature (e.g. 37° C.) for an appropriate period (e.g. 60 min.) with oligo (dT), $MgCl_2$ (e.g. 5 mM), NaCl (e.g. 30 mM), mercaptoethanol (e.g. 5 mM) and Tris-HCl buffer (e.g. pH 8.0, 40 mM) using a reverse transcriptase together with deoxyadenosine triphosphate (dATP), deoxythymidine triphosphate (dTTP), deoxyguanosine triphosphate (dGTP) and deoxycytidine triphosphate (dCTP) (e.g. 0.5 mM each) as substrates.

The thus obtained reaction product is subjected to deproteinization with, for example, phenol, and the template RNA is removed by alkali or ribonuclease treatment. A double stranded DNA is synthesized by a reverse transcriptase in a similar way as the synthesis of the DNA showing complementarity to mRNA described above except that mRNA is replaced by DNA and oligo(dT) is omitted.

By using *Escherichia coli* DNA polymerase I which can be obtained from *Escherichia coli* MRE 600, or the like, instead of reverse transcriptase, the same double stranded DNA can be synthesized.

After the double stranded DNA which is synthesized by the above described procedure is treated with Nuclease $S_1$ which can be obtained from *Aspergillus oryzae* in the presence of $ZnCl_2$ (e.g. 1 mM), sodium acetate buffer (e.g. 0.1 M, pH 4.5), NaCl (e.g. 0.2 M), etc., deoxyadenine chains are formed at both 3' ends of the synthesized DNA by incubating with a terminal transferase purified from calf thymus in the presence of potassium cacodylate buffer (e.g. pH 7.6, 0.14 M), Tris (base) (e.g. 0.03 M), dithiothreitol (e.g. 0.1 mM), $CoCl_2$ (e.g. 1 mM) and dATP (e.g. 1 mM) at an appropriate temperature (e.g. 37° C.) for an appropriate period (e.g. 20 min.)

On the other hand, a plasmid DNA which is used as a vector DNA, e.g. *Escherichia coli* plasmid pBR322 DNA [Gene vol. 2, p. 95-113 (1977)], is cleaved at one site by treating with a restriction endonuclease EcoRI, which can be obtained, for example, from *Escherichia coli* RY13, in the presence of Tris HCl buffer (e.g. pH 7.5, 10 mM), $MgCl_2$ (e.g. 6 mM), NaCl (e.g. 0.1 M), mercaptoethanol (e.g. 6 mM), or the like and then treated with phage λ-derived exonuclease, which can be obtained, for example, from *Escherichia coli* W3102 (λ cI851)×13), in the presence of Na-glycine buffer (e.g. pH 9.5, 0.1 M), $MgCl_2$ (e.g. 5 mM), or the like. Thereafter deoxythymidine chains are formed at both 3' ends in the same way as for the above-described synthesized double stranded DNA by using dTTP instead of dATP.

Synthetic double stranded DNA and plasmid DNA which are chain-elongated at both 3' ends as described above are incubated at an appropriate temperature for an appropriate period with Tris-HCl buffer (e.g. pH 7.5, 50 mM), NaCl (e.g. 0.1 M), EDTA (e.g. 5 mM), or the like and hybridized with hydrogen bonds formed by adenine and thymine. Then, a transformable *Escherichia coli* strain, e.g. *Escherichia coli* χ1776 (Molecular Cloning of Recombinant DNA, Scott, W. A. & Werner, R. edited, Academic Press p. 99-114, 1977) is transformed with the hybridized DNA by the method of Enea et al. (J. Mol. Biol. vol. 96, p. 495-509, 1975) or the like.

In the novel recombinant plasmid DNA thus obtained, there exists a vector. DNA gene, e.g. β-lactamase (enzyme that destroys ampicillin) gene, of *Escherichia coli* plasmid pBR322. Therefore, the transformed *Escherichia coli* shows resistance to ampicillin. The following technique is used to pick up a strain with a novel recombinant having a gene which shows complementarity to the human interferon messenger RNA among these ampicillin resistant strains.

First, [$^{32}$P] labelled DNA is synthesized with the RNA having interferon mRNA activity described above as a template and the DNA is hybridized with mRNA extracted, without induction by poly(I): poly(C) (therefore, interferon mRNA synthesis is not induced), from the human fibroblasts by incubating at a high temperature (e.g. 65° C.) in a reaction mixture containing, for example NaCl (e.g. 0.5 M). Then, the hybridized DNA (Probe A) and non-hybridized DNA (Probe B) are separated by hydroxyapatite column chromatography. Next, filter-fixed DNAs of transformants are hybridized separately with Probe B or Probe A according to the technique of Grunstein-Hogness (Proc. Nat. Acad. Sci. USA, vol. 72, p. 3961-3965, 1975) and strains having a DNA hybridizable with Probe B but not or barely with Probe A are discerned by autoradiography.

Then, plasmid DNA is isolated from each of the discriminated strains and hybridized with mRNA having interferon mRNA activity by incubating at a high temperature (e.g. 53° C.) in the presence of 80% (w/v) formamide, 0.4 M NaCl, etc. Since the mRNA hybridized with cDNA portion of the plasmid DNA from the above-described strain can be retained on a nitrocellulose filter, whereas unhybridized mRNA can not under certain conditions (refer to Example below and Nygaard, A. P. & Hall, B. D., Biochem. Biophys. Res. Commun. Vol. 12, p. 98-104, 1963) this mRNA can be recovered selectively from the filter at a high temperature (e.g. 60° C.) in a solution such as 90% (v/v) formamide and thereafter injected into oocytes of *Xenopus laevis*.

When interferon is synthesized in the oocytes, the DNA used for hybridization must contain a DNA which is complementary to interferon mRNA; and by this method, a recombinant plasmid DNA having a gene showing complementarity to the human fibroblast interferon mRNA can be isolated.

The recombinant plasmid DNA obtained above or segments cleaved with a restriction endonuclease are labelled with a radio isotope such as $^{32}$P by Nick-translation method (Rigby, et al., J. Mol. Biol. vol. 113, p. 237-251, 1977), or the like, and used as a probe to obtain *Escherichia coli* strains containing a recombinant plasmid having the interferon mRNA sequence from the above ampicillin resistant strains in the same way as described above. Several strains thus obtained are cultured and the plasmid DNA is isolated therefrom. The plasmid DNA is cleaved with a restriction endonuclease to obtain the inserted DNA. The length of the inserted DNA is investigated to obtain a plasmid having an inserted DNA coding the entire region of the interferon protein. Primary structure of the inserted DNA of one of recombinant plasmids isolated by the above method is determined according to the Maxam-Gilbert method (Proc. Nat. Acad. Sci. U.S.A. vol. 74, p. 560-564, 1977) and is illustrated in the following Example. It has thus been shown that the recombinant plasmid of the invention contains the entire coding region of the human fibroblast interferon mRNA.

As outlined above, a DNA which codes for human fibroblast interferon polypeptide, especially a DNA which encompasses the entire coding region of the human fibroblast interferon mRNA, a recombinant plasmid containing the DNA and a microorganism containing the plasmid are prepared.

The base sequence of the DNA obtained above and the corresponding peptide sequence are illustrated in Table 5 below.

The base sequence in Table 5 is a preferred example for the expression of the DNA which codes for human interferon polypeptide. Since the amino acids in the peptide sequence in Table 5 may be coded for by a base triplet other than those in Table 5, base sequences of the DNA which codes for human interferon polypeptide other than that in Table 5 are also included in the present invention.

The determination of the base sequence of the DNA which codes for human interferon polypeptide according to the present invention has enabled the chemical synthesis of such DNA.

The present novel recombinant plasmids having a gene which encompasses at least the entire coding region of the human fibroblast interferon mRNA are very useful because they enable mass production of interferon in *Escherichia coli* or in eukaryotic cells which can be grown on a large scale.

Recombinant plasmids containing a DNA using, as a template, leucocyte mRNA or immune interferon mRNA can be prepared by the same method as mentioned above and such plasmids are also expected to be useful for the mass production of interferon.

One specific embodiment of the present invention is illustrated by the following representative example.

Example

After priming of human fibroblasts by overnight incubation with MEM culture medium (product of Nissui Seiyaku Co., Ltd., Japan) containing human interferon which is prepared according to the method described in Proc. Nat. Acad. Sci. USA, 73, 520-523 (1976) (25 U/ml), the fibroblasts were superinduced by adding 10 μg/ml of poly(I): poly(C) (product of Galbiochem Co., USA) and 5 μg/ml of cycloheximide to the medium. The priming and superinduction are carried out according to the methods described in Brit. J. Exp. Path., 39, 452-458 (1958) and Antimicrob. Agents Chemother., 2, 476-484 (1972), respectively.

After 4 hours, $1.5 \times 10^9$ superinduced human fibroblasts were destroyed by Teflon homogenizer (sold by Takashima Shoten Co., Japan) at a temperature of 0 to 4° C. in the presence of 0.3% NP-40 (product of Daiichi Kagaku Co., Japan) and 50 μg/ml heparin in RSB buffer (10 mM Tris-HCl, pH 7.5; 10 mM NaCl; 1.5 mM $MgCl_2$). Nuclei were removed by centrifugation at 3000 rpm and 4° C. for 10 minutes and 9.6 mg of cytoplasmic RNA was obtained by extraction 3 times with phenol.

The cytoplasmic RNA was precipitated with 67% ethanol in the presence of 0.1M NaCl, dissolved in 10 ml of 1 mM EDTA solution and incubated at 65° C. for 2 minutes. Then, 2.5 ml of a salt solution at a high concentration (0.5 M Tris-HCl, pH 7.5; 1 M NaCl; 50 mM EDTA) was added to the above solution and the mixture was put on a column packed with 0.15 g of an oligo(dT) cellulose (product of P-L Biochemicals Co., USA) to adsorb mRNA containing poly(A). Elution was then carried out with a salt solution at a low concentration (10 mM Tris-HCl, pH 7.5) and water to isolate 250 μg of mRNA containing poly(A).

The mRNA was precipitated with 67% ethanol in the presence of 0.1M NaCl and dissolved in 0.5 ml of 1 mM EDTA solution. The solution was incubated at 65° C. for 2 minutes, subjected to centrifugation through a 5-25% sucrose-density gradient containing 50 mM Tris-HCl, pH 7.5, 0.2 M NaCl and 1 mM EDTA (rotated at 35,000 rpm using the SW40 rotor of Beckmann Co., U.S.A.) at 4° C. for 16 hrs. and fractionated into 20 fractions.

The interferon mRNA activity of each of these fractions was determined as mentioned above, and the results are shown in Table 1 below.

TABLE 1

| Fraction No. | Interferon Activity |
|---|---|
| 9 | <50 units/ml |
| 10 | 44 |
| 11 | 550 |
| 12 | 52 |

The mRNA in Fraction No. 11 was approximately 5 This mRNA and a reverse transcriptase were incubated at 37° C. for an hour in 20 μl of a reaction mixture consisting of 5 μg mRNA; 0.5 mM dATP; 0.5 mM dTTP; 0.5 mM dGTP; 0.5 mM dCTP; 1 μg oligo (dT) (product of P-L Biochemicals Co., USA); 8 units reverse transcriptase (derived from Avian Myeloblastosis Virus, for example: product of Life Science Inc. Florida, USA); 5 mM $MgCl_2$; 30 mM NaCl; 5 mM mercaptoethanol; and 40 mM Tris-HCl (pH 8.0) and then deproteinized with phenol. After RNA was removed by treatment with 0.3 N NaOH at 37° C. for 15 hours, the synthesized single stranded DNA was incubated at 37° C. in 20 μl of a reaction mixture [the same mixture as described above except that mRNA and oligo (dT) were omitted] for one hour to synthesize 1.5 μg of a double stranded DNA.

The double stranded DNA was treated with Nuclease $S_1$ (product of Bethesda Research Laboratories Inc., USA which is referred to as BRL, hereinafter) in 50 μl of a reaction mixture (1.5 μg double stranded DNA: 1 mM $ZnCl_2$; M sodium acetate, pH 4.5; 0.2 M NaCl; 0.05 unit $S_1$) at 37° C. for 30 minutes and the enzyme was removed by phenol extraction. The DNA was precipitated with ethanol and then treated with a terminal transferase in 20 μl of a reaction mixture consisting of 1.5 μg DNA; 0.14 M potassium cacodylate, pH 7.6; 0.03 M Tris (base); 0.1 mM dithiothreitol; 1 mM $CoCl_2$; 1 mM dATP; and 1 unit terminal transferase (product of BRL) at 37° C. for 20 minutes to obtain about 1.5 μg of a product wherein 100 deoxyadenosine chains were formed at both 3' ends of the double-stranded DNA.

On the other hand, 10 μg of *Escherichia coli* plasmid pBR322 DNA (product of BRL) was treated at 37° C. for 2 hours with a restriction endonuclease EcoRI in 100 μl of a reaction mixture consisting of 10 mM Tris-HCl, pH 7.5; 6 mM $MgCl_2$; 0.1 M NaCl; 6 mM mercaptoethanol; and 10 units EcoRI (product of BRL) leading to the cleavage at the only one cutting site in pBR322 DNA. The cut plasmid DNA was treated with an exonuclease derived from phage λ in 200 μl of a reaction mixture consisting of 10 μg DNA; 0.1 M Na-glycine, pH 9.5; 5 mM $MgCl_2$; 50 μg/ml albumin (product of Merck & Co., USA); and 17.5 units λ exonuclease (product of Miles Laboratories Inc., USA) at 0° C. for 90 minutes and the enzyme was removed by phenol extraction. The DNA was treated with a terminal transferase in 50 µl of a reaction mixture [10 µg DNA; 0.14 M potassium cacodylate, pH 7.6; 0.03 M Tris (base); 0.1 mM dithiothreitol; 1 mM $CoCl_2$; 1 mM dTTP; 2 units terminal transferase] at 37° C. for 20 minutes to obtain about 0.5 µg of a product wherein 100 deoxythymidine chains were formed at both 3' ends of plasmid pBR322 DNA described above.

Then, 0.02 µg of the synthesized double stranded DNA obtained above, and 0.1 µg of the plasmid pBR322 DNA were incubated for hybridization in a solution containing 0.1 M NaCl, 50 mM Tris-HCl (pH 7.5) and 5 mM EDTA at 65° C. for 2 minutes, at 45° C. for one hour, at 37° C. for one hour and at room temperature for one hour. Then, *Escherichia coli* χ1776 was transformed with the hybridized recombinant following the method of Enea et al.

About 4,000 ampicillin-resistant strains were isolated by this method. 3,600 resistant strains were chosen, and the DNA of each strain was fixed on nitrocellulose filters in duplicate (Grunstein-Hogness Method).

On the other hand, [$^{32}$P] labelled single stranded DNA was synthesized (about 0.44 µg, specific radioactivity approx. 6×10$^8$ c.p.m./µg) by a reverse transcriptase in the same way as that for single stranded DNA mentioned above (dCTP was labelled with $^{32}$P) using the interferon mRNA fraction (about 10 µg) which had been extracted and partially purified as described above, as a template. The DNA was hybridized in 50 µl of a reaction mixture (25 µg mRNA; 0.45 µg single stranded DNA labelled with $^{32}$P; 0.5 M NaCl; 25 mM Pipes buffer, pH 6.5) at 65° C. for 40 hours with 25 µg of mRNA extracted from human fibroblasts which had not been induced by poly(I): poly(C). The latter mRNA was prepared by the same method used to extract poly(I): poly(C)-induced mRNA. The reaction mixture was put on a column packed with 0.2 g of a hydroxyapatite, and elution was first carried out with 5 ml of 0.14 M phosphate buffer (pH 6.5) to elute the single stranded DNA, and then with 5 ml of 0.4 M phosphate buffer to elute the DNA hybridized with RNA. As the result, the DNA (about 90% of the whole) (Probe A) which hybridized with the mRNA mentioned above, and the DNA (about 10% of the whole) (Probe B) which did not hybridize were isolated.

Each probe was then hybridized separately with the above DNA fixed on the nitrocellulose filters according to the Grunstein-Hogness method. Four strains were identified which reacted mainly to Probe B but little to Probe A by autoradiography.

Table 2 shows the extent of reaction of the DNAs from the four strains to each probe as revealed by auto-radiogram.

TABLE 2

| Ampicillin-resistant strains | Extent of Reaction of Probe with DNA in the strains | |
|---|---|---|
| | Probe A | Probe B |
| #319 | + + | + + + + |
| #644 | + | + + + |
| #746 | − | + + |
| #3578 | + | + + + + + |

Plasmid DNA was isolated from cells of the four strains by the method of Currier and Nester (Analyt. Biochem. vol. 76, p. 431-441, 1976). Then, these DNAs were hybridized with the interferon mRNA as follows.

First, 5 µg of plasmid DNA was linearized by incubating with restriction endonuclease Hind III which can be obtained from *Haemophilus influenzae* Rd in 50 µl of a reaction mixture consisting of 10 mM Tris-HCl, pH 7.5; 6 mM $MgCl_2$; 50 mM NaCl; 6 mM mercaptoethanol; and 5 units Hind III (product of BRL) at 37° C. for 2 hours. After deproteinization by phenol extraction, the DNA was precipitated with ethanol and dissolved in 20 µl of 80% (w/v) formamide. The solution was denatured at 85° C. for 10 minutes and was then incubated in a solution consisting of 2.5 µg mRNA, 20 µl 80% (w/v) formamide, 20 mM Pipes buffer (pH 6.5), 0.4 M NaCl and 5 mM EDTA, at 53° C. Four hours later the mixture was mixed with 0.4 ml of 3×SSC (1×SSC corresponds to 0.15 M NaCl, 0.015 M sodium citrate) at 0° C., and was filtered through a nitrocellulose filter (diameter: 1 cm, pore size: 0.45 µm) at a rate of about 0.5 ml per minute. After washing the filter with about 1.5 ml of 2×SSC, the filter was immersed in a solution consisting of 0.6 ml of 90% (v/v) formamide, 20 mM Pipes buffer, 0.1% SDS (sodium dodecylsulfate) and 5 mM EDTA. Incubation of the filter at 60° C. for 2 minutes and the removal of the solution were repeated 3 times and the RNA eluted from the nitrocellulose filter into the solution (1.8 ml) was precipitated with ethanol in the presence of 0.1 M NaCl. The mRNA containing poly(A) was isolated from the RNA by using oligo(dT) cellulose column chromatography, dissolved in a mixture of 3 µl of 10 mM Tris-HCl (pH 7.5) and 88 mM NaCl and injected into the oocytes of *Xenopus laevis*. After 15 hours, the interferon synthesized in the oocytes was determined (antiviral activity).

Table 3 shows the interferon mRNA activity of the mRNA which has hybridized with the DNA derived from the four bacterial strains mentioned above.

TABLE 3

| Bacterial strain | Interferon mRNA activity (unit/ml) |
|---|---|
| #319 | 360 |
| #644 | <10 |
| #746 | 15 |
| #3578 | <10 |
| pBR322DNA | <10 |

Five µg of plasmid DNA obtained from strain #319 by the Currier and Nester method was cleaved with restriction endonuclease Hind III in the same manner as mentioned above. The DNA and the recombinant plasmid βGpBR322 DNA (the vector was pBR322) (obtained from the Institute for Molecular Biology I of University of Zurich or prepared by the method described in Nature 281, 40-46, 1979) containing rabbit β-globin gene, separately or as a mixture, were hybridized with a mixture of rabbit globin mRNA (obtained from rabbit red blood cells) (1 µg) and interferon mRNA (2.5 µg) obtained from human fibroblasts under the same conditions as mentioned above. The mRNA which formed a hybrid was injected into the oocytes of *Xenopus laevis*. The oocytes were then incubated for 15 hours in Barth's culture medium (J. Embryol. Exp. Morph. 7, 210, 1959) containing [$^3$H] labelled histidine and [$^3$H] labelled globin was isolated by acrylamide gel electrophoresis and determined quantitatively by fluorography according to the method described in Eur. J. Biochem. 46, 83-88, (1974). The interferon was determined by antiviral activity as described above. The synthesis of rabbit β-globin and the human interferon was determined in this way. The result is shown in Table 4 below.

TABLE 4

| DNA | Synthesized interferon activity | Amount of globin synthesized |
|---|---|---|
| #319 | 200 (units/ml) | – |
| GpBR322 | 35 | + + + + |
| mixture of both plasmids | 160 | + + + |

From the result of this experiment it has been established that DNA of #319 has DNA (the interferon gene) which forms a hybrid specifically with the interferon mRNA.

The DNA of #319 was cleaved with several restriction endonucleases and a restriction endonuclease map, FIG. 1(a), was made by agarose gel electrophoresis.

Figure 1B:
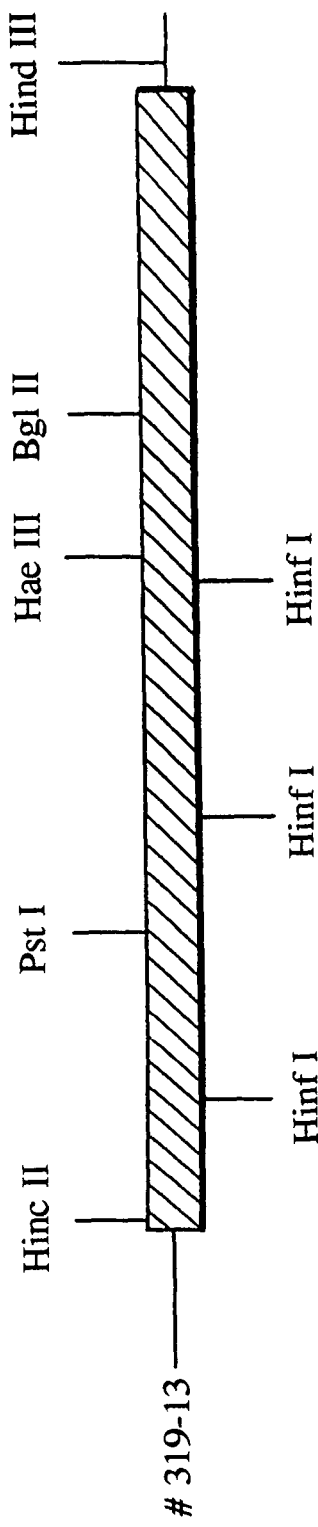

Restriction endonucleases, Pst I, Bgl II and Hind III (sold by BRL, etc.) cleave #319 DNA at the sites illustrated in FIG. 1 (a).

The segments obtained by cleaving #319 DNA with restriction endonucleases Pst I and Bgl II were isolated and purified by gel electrophoresis according to the method of Tabak & Flavell (Nucleic Acids Research, vol. 5, p. 2321-2332, 1978). The segments were labelled with $^{32}P$ according to the method of Rigby, et al. (J. Mol. Biol. vol. 113, p. 237-251, 1977) and the labelled segment was used as a probe. Several strains containing a plasmid which shows complementarity to the probe were isolated from the above ampicillin-resistant strains according to the above method of Grunstein & Hogness (Proc. Nat. Acad. Sci. U.S.A., vol. 72, p. 3961-3965, 1975), namely, colony hybridization method. Plasmid DNAs were obtained from each of the strains according to the above method of Currier-Nester and the inserted portions thereof were cleaved with a restriction endonuclease such as Hind III. The cut plasmid DNA segments were compared in length and the longest plasmid DNA segment was selected. The plasmid was named 4319-13.

The restriction endonuclease map of the plasmid is illustrated in FIG. 1 (b) which substantiates that the novel plasmid has an mRNA sequence containing the mRNA sequence of #319. Primary structure (base sequence) of the mRNA sequence inserted in the plasmid of #319-13 was determined by the method of Maxam-Gilbert (Proc. Nat. Acad. Sci, U.S.A. vol. 74, p. 560-564, 1977). The primary structure is given in Table 5 below.

TABLE 5

```
                -20                                         -10                                          1
        MET THR ASN LYS CYS LEU LEU GLN ILE ALA LEU LEU LEU CYS PHE SER THR THR ALA LEU SER MET SER TYR
GTC AAC ATG ACC AAC AAG TGT CTC CTC CAA ATT GCT CTC CTG TTG TGC TTC TCC ACT ACA GCT CTT TCC ATG AGC TAC
CAG TTG TAC TGG TTG TTC ACA GAG GAG GTT TAA CGA GAG GAC AAC ACG AAG AGG TGA TGT CGA GAA AGG TAC TCG ATG
                    20                                  40                                  60

10                                          20
ASN LEU LEU GLY PHE LEU GLN ARG SER SER ASN PHE GLN CYS GLN LYS LEU LEU THR GLY LEU ASN GLY ARG LEU GLU
AAC TTG CTT GGA TTC CTA CAA AGA AGC AGC AAT TTT CAG TGT CAG AAG CTC CTG TGG CAA TTG AAT GGG AGG CTT GAA
TTG AAC GAA CCT AAG GAT GTT TCT TCG TCG TTA AAA GTC ACA GTC TTC GAG GAC ACC GTT AAC TTA CCC TCC GAA CTT
80                          100                         120                         140

30                              40                              50
TYR CYS LEU LYS ASP ARG MET ASN PHE ASP ILE PRO GLU GLU ILE LYS GLN LEU GLN GLN PHE GLN LYS GLU ASP ALA
TAT TGC CTC AAG GAC AGG ATG AAC TTT GAG ATC CCT GAG GAG ATT AAG CAG CTG CAG CAG TTC CAG AAG GAG GAC GCC
ATA ACG GAG TTC CTG TCC TAC TTG AAA CTC TAG GGA CTC CTC TAA TTC GTC GAC GTC GTC AAG GTC TTC CTC CTG CGG
    160                         180                         200                         220

60                              70                              80
ALA LEU THR ILE TYR GLU MET LEU GLN ASN ILE PHE ALA ILE PHE ARG GLN ASP SER SER SER THR GLY TRP ASN GLU
GCA TTG ACC ATC TAT GAG ATG CTC CAG AAC ATC TTT GCT ATT TTC AGA CAA GAT TCA TCT AGC ACT GGC TGG AAT GAG
CGT AAC TGG TAG ATA CTC TAC GAG GTC TTG TAG AAA CGA TAA AAG TCT GTT CTA AGT AGA TCG TGA CCG ACC TTA CTC
    240                         260                         280                         300

90                              100
THR ILE VAL GLU ASN LEU LEU ALA ASN VAL TYR HIS GLN ILE ASN HIS LEU LYS THR VAL LEU GLU GLU LYS LEU GLU
ACT ATT GTT GAG AAC CTC CTG GCT AAT GTC TAT CAT CAG ATA AAC CAT CTG AAG ACA GTC CTG GAA GAA AAA CTG GAG
TGA TAA CAA CTC TTG GAG GAC CGA TTA CAG ATA GTA GTC TAT TTG GTA GAC TTC TGT CAG GAC CTT CTT TTT GAC CTC
    320                         340                         360                         380

110                             120                             130
LYS GLU ASP PHE THR ARG GLY LYS LEU MET SER SER LEU HIS LEU LYS ARG TYR TYR GLY ARG ILE LEU HIS TYR LEU
AAA GAA GAT TTC ACC AGG GGA AAA CTC ATG AGC AGT CTG CAC CTG AAA AGA TAT TAT GGG AGG ATT CTG CAT TAC CTG
TTT CTT CTA AAG TGG TCC CCT TTT GAG TAC TCG TCA GAC GTG GAC TTT TCT ATA ATA CCC TCC TAA GAC GTA ATG GAC
            400                             420                             440                             460

140                             150
LYS ALA LYS GLU TYR SER HIS CYS ALA TRP THR ILE VAL ARG VAL GLU ILE LEU ARG ASN PHE TYR PHE ILE ASN ARG
AAG GCC AAG GAG TAC AGT CAC TGT GCC TGG ACC ATA GTC AGA GTG GAA ATC CTA AGG AAC TTT TAC TTC ATT AAC AGA
TTC CGG TTC CTC ATG TCA GTG ACA CGG ACC TGG TAT CAG TCT CAC CTT TAG GAT TCC TTG AAA ATG AAG TAA TTG TCT
                    480                             500                             520                             540

160                     166
LEU THR GLY TYR LEU ARG ASN
CTT ACA GGT TAC CTC CGA AAC TGA AGA TCT CCT AGC CTG TGC CTC TGG GAC TGG ACA ATT GCT TCA ACG ATT CTT CAA
GAA TGT CCA ATG GAG GCT TTG ACT TCT AGA GGA TCG GAC ACG GAG ACC CTG ACC TGT AAA CGA AGT TCG TAA GAA GTT
                    560                             580                             600                             620

CCA GCA GAT GCT GTT TAA GTG ACT GAT GGC TAA TGT ACT GCA TAT GAA AGG ACA CTA GAA GAT TTT GAA ATT TTT ATT
GGT CGT CTA CGA CAA ATT CAC TGA CTA CCG ATT ACA TGA CGT ATA CTT TCC AGT GAT CTT CTA AAA CTT TAA AAA TAA
            640                         660                         680                         700
```

TABLE 5-continued

```
AAA TTA TGA GTT ATT TTT ATT TAT TTA AAT TTT ATT TTG GAA AAT AAA TTA TTT TTG GTG CAA AAG TCA AAA AAA
TTT AAT ACT CAA TAA AAA TAA ATA AAT TTA AAA TAA AAC CTT TTA TTT AAT AAA AAC CAC GTT TTC AGT TTT TTT
                        720                 740                         760
```

The DNA sequence permits prediction of the entire amino acid sequence for human fibroblast interferon (amino acids 1-166) and its putative signal peptide (amino acids -21 to -1) as shown in the line above the DNA sequences.

It is important that in the sequence there exist without any errors the base sequence (three base pairs) corresponding to the amino acid sequence from the amino-terminal to 13th amino acid of the human fibroblast interferon reported by Knight, et al. (Science vol. 207, p. 525-526, 1980). This fact establishes that the #319-13 plasmid of the present invention has the human fibroblast interferon mRNA sequence.

Further, it is apparent from the data of the primary sequence that the plasmid encompasses the entire coding region of the protein of the above mRNA and probably the coding region of the signal peptide.

Therefore, transformation of the plasmid or mRNA inserted therein to other expression plasmids enables a host such as *Escherichia coli* to produce interferon. For such purposes, the #319-13 plasmid which is named TpIF 319-13, transformed in *Escherichia coli* X1776, has been deposited with the American Type Culture Collection, Rockville. Md., U.S.A. (now located at P.O. Box 1549, Manassas. Va. 20108. U.S.A.), under accession number ATCC 31712 and is freely available to the public.

What is claimed is:

1. A human fibroblast $\beta_1$ interferon polypeptide produced by the process comprising: expressing an expression plasmid in a host cell, said plasmid comprising a DNA sequence coding for human fibroblast $\beta_1$ interferon, whereby expression of human fibroblast $\beta_1$ interferon by a host is enabled, and recovering said interferon.

2. Recombinant human fibroblast $\beta_1$ interferon.

3. Recombinant human fibroblast $\beta_1$ interferon having the amino acid sequence:
Met Ser Tyr Asn Leu Leu Gly Phe Leu Gln Arg Ser Ser Asn Phe Gln Cys Gln Lys Leu Leu Trp Gln Leu Asn Gly Arg Leu Glu Tyr Cys Leu Lys Asp Arg Met Asn Phe Asp Ile Pro Glu Glu Ile Lys Gln Leu Gln Gln Phe Gln Lys Glu Asp Ala Ala Leu Thr Ile Tyr Glu Met Leu Gln Asn Ile Phe Ala Ile Phe Arg Gln Asp Ser Ser Ser Thr Gly Trp Asn Glu Thr Ile Val Glu Asn Leu Leu Ala Asn Val Tyr His Gln Ile Asn His Leu Lys Thr Val Leu Glu Glu Lys Leu Glu Lys Glu Asp Phe Thr Arg Gly Lys Leu Met Ser Ser Leu His Leu Lys Arg Tyr Tyr Gly Arg Ile Leu His Tyr Leu Lys Ala Lys Glu Tyr Ser His Cys Ala Trp Thr Ile Val Arg Val Glu Ile Leu Arg Asn Phe Tyr Phe Ile Asn Arg Leu Thr Gly Tyr Leu Arg Asn.

4. Recombinant human fibroblast $\beta_1$ interferon having the amino acid sequence:
Met Thr Asn Lys Cys Leu Leu Gln Ile Ala Leu Leu Leu Cys Phe Ser Thr Thr Ala Leu Ser Met Ser Tyr Asn Leu Leu Gly Phe Leu Gln Arg Ser Ser Asn Phe Gln Cys Gln Lys Leu Leu Trp Gln Leu Asn Gly Arg Leu Glu Tyr Cys Leu Lys Asp Arg Met Asn Phe Asp Ile Pro Glu Glu Ile Lys Gln Leu Gln Gln Phe Gln Lys Glu Asp Ala Ala Leu Thr Ile Tyr Glu Met Leu Gln Asn Ile Phe Ala Ile Phe Arg Gln Asp Ser Ser Ser Thr Gly Trp Asn Glu Thr Ile Val Glu Asn Leu Leu Ala Asn Val Tyr His Gln Ile Asn His Leu Lys Thr Val Leu Glu Glu Lys Leu Glu Lys Glu Asp Phe Thr Arg Gly Lys Leu Met Ser Ser Leu His Leu Lys Arg Tyr Tyr Gly Arg Ile Leu His Tyr Leu Lys Ala Lys Glu Tyr Ser His Cys Ala Trp Thr Ile Val Arg Val Glu Ile Leu Arg Asn Phe Tyr Phe Ile Asn Arg Leu Thr Gly Tyr Leu Arg Asn.

5. A composition comprising water and a nonglycosylated mature human fibroblast interferon polypeptide having a total of 166 amino acids and the following amino acid sequence:
X-Ser-Tyr-Asn-Leu-Leu-Gly-Phe-Leu-Gln-Arg-Ser-Ser-Asn-Phe-Gln-Cys-Gln-Lys-Leu-Leu-Trp-Gln-Leu-Asn-Gly-Arg-Leu-Glu-Tyr-Cys-Leu-Lys-Asp-Arg-Met-Asn-Phe-Asp-Ile-Pro-Glu-Glu-Ile-Lys-Gln-Leu-Gln-Gln-Phe-Gln-Lys-Glu-Asp-Ala- Ala-Leu-Thr-Ile-Tyr-Glu-Met-Leu-Gln-Asn-Ile-Phe-Ala-Ile-Phe-ArgGln-Asp-Ser-Ser-Ser-Thr-Gly-Trp-Asn-Glu-Thr-Ile-Val-Glu-Asn-Leu-Leu-Ala-Asn-Val-Tyr-His-Gln-Ile-Asn-His-Leu-Lys-Thr-Val-Leu-Glu-Glu-Lys-Leu-Glu-Lys-Glu-Asp- Phe-Thr-Arg-Gly-Lys-Leu-Met-Ser-Ser-Leu-His-Leu-Lys-Arg-Tyr-Tyr-Gly-Arg-Ile-Leu-HisTyr-Leu-Lys-Ala-Lys-Glu-Tyr-Ser-His-Cys-Ala-Trp-Thr-Ile-Val-Arg-Val-Glu-Ile-Leu-Arg-Asn-Phe-TyrPhe-Ile-Asn-Arg-Leu-Thr-Gly-Tyr-Leu-Arg-Asn,
wherein X is Met; said composition being free of any glycosylated human fibroblast interferon.

6. The composition of claim 5, which is free of human proteins.

7. Recombinant, mature human fibroblast interferon $\beta_1$ which is free of any glycosylated human fibroblast interferon.

8. Recombinant, human fibroblast interferon having a total of 166 amino acids and produced by expression in *E. coli* of an expression plasmid comprising the following DNA sequence coding for human fibroblast interferon operably linked therein for expression by an *E. coli* host:

```
ATG AGC TAC AAC TTG CTT GGA TTC CTA CAA AGA AGC AGC AAT TTT CAG
TAC TCG ATG TTG AAC GAA CCT AAG GAT GTT TCT TCG TCG TTA AAA GTC

TGT CAG AAG CTC CTG TGG CAA TTG AAT GGG AGG CTT GAA TAT TGC CTC
ACA GTC TTC GAG GAC ACC GTT AAC TTA CCC TCC GAA CTT ATA ACG GAG

AAG GAC AGG ATG AAC TTT GAC ATC CCT GAG GAG ATT AAG CAG CTG CAG
TTC CTG TCC TAC TTG AAA CTG TAG GGA CTC CTC TAA TTC GTC GAC GTC

CAG TTC CAG AAG GAG GAC GCC GCA TTG ACC ATC TAT GAG ATG CTC CAG
GTC AAG GTC TTC CTC CTG CGG CGT AAC TGG TAG ATA CTC TAC GAG GTC
```

```
AAC ATC TTT GCT ATT TTC AGA CAA GAT TCA TCT AGC ACT GGC TGG AAT
TTG TAG AAA CGA TAA AAG TCT GTT CTA AGT AGA TCG TGA CCG ACC TTA

GAG ACT ATT GTT GAG AAC CTC CTG GCT AAT GTC TAT CAT CAG ATA AAC
CTC TGA TAA CAA CTC TTG GAG GAC CGA TTA CAG ATA GTA GTC TAT TTG

CAT CTG AAG ACA GTC CTG GAA GAA AAA CTG GAG AAA GAA GAT TTC ACC
GTA GAC TTC TGT CAG GAC CTT CTT TTT GAC CTC TTT CTT CTA AAG TGG

AGG GGA AAA CTC ATG AGC AGT CTG CAC CTG AAA AGA TAT TAT GGG AGG
TCC CCT TTT GAG TAC TCG TCA GAC GTG GAC TTT TCT ATA ATA CCC TCC

ATT CTG CAT TAC CTG AAG GCC AAG GAG TAC AGT CAC TGT GCC TGG ACC
TAA GAC GTA ATG GAC TTC CGG TTC CTC ATG TCA GTG ACA CGG ACC TGG

ATA GTC AGA GTG GAA ATC CTA AGG AAC TTT TAC TTC ATT AAC AGA CTT
TAT CAG TCT CAC CTT TAG GAT TCC TTG AAA ATG AAG TAA TTG TCT GAA

ACA GGT TAC CTC CGA AAC
TGT CCA ATG GAG GCT TTG.
```

9. The recombinant, human fibroblast interferon of claim 8 having the amino acid sequence:
Met Ser Tyr Asn Leu Leu Gly Phe Leu Gln Arg Ser Ser Asn Phe Gln Cys Gln Lys Leu Leu Trp Gln Leu Asn Gly Arg Leu Glu Tyr Cys Leu Lys Asp Arg Met Asn Phe Asp Ile Pro Glu Glu Ile Lys Gln Leu Gln Gln Phe Gln Lys Glu Asp Ala Ala Leu Thr Ile Tyr Glu Met Leu Gln Asn Ile Phe Ala Ile Phe Arg Gln Asp Ser Ser Ser Thr Gly Trp Asn Glu Thr Ile Val Glu Asn Leu Leu Ala Asn Val Tyr His Gln Ile Asn His Leu Lys Thr Val Leu Glu Glu Lys Leu Glu Lys Glu Asp Phe Thr Arg Gly Lys Leu Met Ser Ser Leu His Leu Lys Arg Tyr Tyr Gly Arg Ile Leu His Tyr Leu Lys Ala Lys Glu Tyr Ser His Cys Ala Trp Thr Ile Val Arg Val Glu Ile Leu Arg Asn Phe Tyr Phe Ile Asn Arg Leu Thr Gly Tyr Leu Arg Asn.

10. A composition comprising water and the interferon of claim 8.

11. The recombinant, human fibroblast interferon of claim 8 or 9 which is free of any glycosylated human fibroblast interferon.

12. A composition comprising water and the interferon of claim 11.

13. The composition of claim 12 free of human protein.

14. A composition comprising water and the interferon of claim 9.

* * * * *